United States Patent [19]

Kamishioiri et al.

[11] Patent Number: 5,009,651
[45] Date of Patent: Apr. 23, 1991

[54] SURFACE MATERIAL FOR SANITARY ARTICLES AND ITS PREPARING METHOD

[75] Inventors: Nobuyuki Kamishioiri; Manabu Kaneda; Toshiyasu Tanaami; Miho Maeda, all of Tochigi, Japan

[73] Assignee: Kao Corporation, Tokyo, Japan

[21] Appl. No.: 395,579

[22] Filed: Aug. 18, 1989

[30] Foreign Application Priority Data

Sep. 6, 1988 [JP] Japan .................. 63-223282

[51] Int. Cl.⁵ ............................. A61F 13/15
[52] U.S. Cl. ................... 604/378; 604/385.1; 128/155
[58] Field of Search ............ 604/378, 384, 385.1, 604/367

[56] References Cited

U.S. PATENT DOCUMENTS

| | | | |
|---|---|---|---|
| 1,092,082 | 11/1967 | Holiday et al. | 604/384 |
| 3,409,012 | 11/1989 | Seltzer | 604/384 |
| 4,585,449 | 4/1986 | Karami | 604/378 |
| 4,804,378 | 2/1989 | Shiba et al. | 604/367 |
| 4,826,498 | 5/1989 | Koczab | 604/384 |
| 4,865,597 | 9/1989 | Mason, Jr. et al. | 604/378 |
| 4,883,480 | 11/1989 | Huffman et al. | 604/378 |
| 4,892,532 | 1/1990 | Boman | 604/378 |

FOREIGN PATENT DOCUMENTS

| | | |
|---|---|---|
| 54-163136 | 12/1979 | Japan . |
| 54-163137 | 12/1979 | Japan . |
| 55-68367 | 5/1980 | Japan . |
| 57-1339 | 1/1982 | Japan . |
| 57-136454 | 8/1982 | Japan . |
| 58-180602 | 10/1983 | Japan . |
| 59-32456 | 2/1984 | Japan . |
| 59-36534 | 9/1984 | Japan . |
| 62-20194 | 5/1987 | Japan . |
| 2023067 | 12/1979 | United Kingdom . |

Primary Examiner—Randall L. Green
Assistant Examiner—Gina Gualtieri
Attorney, Agent, or Firm—Birch, Stewart, Kolasch & Birch

[57] ABSTRACT

A surface material for sanitary articles is composed of Layer 1, which is located on the surface in contact with the skin, and Layer 2, which is formed into a single unit with Layer 1 underneath Layer 1 with its entire surface being essentially covered by Layer 1, and with Layer 1 being composed of 50% or more hydrophobic fibers and moreover, in which at least the portion of Layer 1 covering Layer 2 possesses Section A of which the fiber density is comparatively low, Section B of which the fiber density is comparatively high, and Section C which is located at their boundary, where the area of Section C occupies 2-50% of the area of the entire surface material.

11 Claims, 3 Drawing Sheets

SURFACE MATERIAL FOR SANITARY ARTICLES AND ITS PREPARING METHOD

This invention relates to a surface material that can be favorably used in general on sanitary articles such as disposable absorbent products, etc. More specifically, this invention relates to a surface material that is extremely pleasant to the user which can be favorably used on sanitary articles such as sanitary napkins, disposable diapers and sanitary pads.

BACKGROUND OF THE INVENTION

It is commonly known that the structure of absorbent products which are used in order to absorb and retain liquids that are produced from the body involves an absorber, which absorbs and retains liquids, interposed between a surface material, which is permeable to liquids, and a leak-proof material, which is impermeable to liquids. In such absorbent products, aside from the obvious characteristic of quickly transferring the liquid to be absorbed to the absorber, it is necessary that the liquid-permeable surface material (which is also sometimes referred to as the outer wrapping, covering, top sheet or cover stock) does not give an unpleasant feeling to the user by not allowing backflow of the liquid that has moved into the absorber (to be referred to as backflow prevention), does not give an unpleasant feeling to the user by not allowing the surface to become stained when absorbing colored liquids such as fecal material or blood (to be referred to as stain prevention), does not allow the liquid that has been absorbed into the absorber to leak from the ends of the sanitary article through the surface material, and also provide adequate ventilation.

In order to achieve this objective, various proposals have been made and techniques to improve upon these proposals are also numerous.

Specifically, to begin with, instead of hydrophilic materials such as pulp or rayon which have been typically used in the past for the component materials of the surface material, there is an example of the prior art which improves the prevention of backflow by the formation of a region of hydrophobic atmosphere between the surface of the body and the absorber using hydrophobic synthetic fibers such as polyolefine and polyester (Pat. Disclosure SHO 58-180602). Although backflow prevention is improved considerably as a result of this, there is an inevitable occurrence of a reduction in liquid permeability.

Therefore, although techniques have been proposed which allow both liquid permeability and backflow prevention to co-exist by composing the surface material blending both hydrophobic fibers and hydrophilic fibers (Pat. Disclosure SHO 55-68367, Pat. Disclosure SHO 57-136454) or using a hydrophobic fiber following hydrophilic treatment of the surface (Pat. Disclosure SHO 54-163136), in these methods, it still remains extremely difficult to make these two properties compatible with each other.

In addition, other techniques have been proposed which attempt to solve the above problems by providing holes in hydrophobic nonwoven fabric or film and placing a hydrophilic fiber beneath it, followed by further allowing the lower hydrophilic fiber to penetrate to the surface of the holed portion (Pat. Disclosure SHO 57-1339, Utility Model SHO 62-20194, and Pat. Journal SHO 59-36534).

However, in the case of actually using such surface materials, when pressure is applied due to movement of the user, since liquid that has migrated to the absorber easily transfers to the body surface, backflow prevention was inadequate. Moreover, since the lower hydrophilic fiber layer is visible through the holes, stain prevention was poor.

On the other hand, although there were also techniques which solved the above problems by extending hydrophilic fibers into a hydrophobic surface material using fluid differential pressure or needle punch, etc. (Pat. Journal SHO 59-32456), since effectively extending the hydrophilic fibers is extremely difficult in consideration of the accompanying complexity of the manufacturing process, the anticipated effectiveness was not obtained.

In this manner, the prior art was unable to obtain a surface material having both superior liquid permeability and backflow prevention, and this became a major obstacle in improving the performance of absorbent products resulting in a solution being hoped for as soon as possible.

BRIEF DESCRIPTION OF THE INVENTION

Therefore, this invention provides a nonwoven fabric to function as a surface material of a sanitary article in which the surface material quickly absorbs excreted liquids, suppresses the phenomenon of backflow of the absorbed liquid, and moreover, restricts any oozing or leaking of absorbed liquid from the edges of the sanitary article, as well as its preparing method.

DETAILED DESCRIPTION OF THE INVENTION

To overcome such problems, the inventors completed this invention successfully creating a surface material with both superior liquid permeability and backflow prevention.

In other words, this invention provides a surface material for sanitary articles which has the characteristic of being composed of Layer 1, which is located on the surface in contact with the skin, and Layer 2, which is formed into a single unit with Layer 1 underneath Layer 1 with its entire surface being essentially covered by Layer 1, and with Layer 1 being composed of 50% or more hydrophobic fibers and moreover, in which at least the portion of Layer 1 covering Layer 2 possesses Section A of which the fiber density is comparatively low, Section B of which the fiber density is comparatively high, and Section C which is located at their boundary, where the area of Section C occupies 2-50% of the area of the entire surface material.

In addition, this invention provides a method of preparing a surface material for sanitary articles which has the characteristic of passing Layer 1, which is located on the surface in contact with the skin and is composed of a fiber aggregate of 50% or more hydrophobic fibers, and Layer 2 located beneath layer 1, which is composed of a fiber aggregate of 50% or more hydrophilic fibers, through an engraving roll in the form of a laminated structure followed by partial compression bonding and/or fusing to give it an embossed pattern.

In describing a suitable form of embodiment of the preparing method of this invention, the main component of Layer 1 is heat-fusing, short fibers with it also being composed of 50% or more hydrophobic fibers. Said fibers are formed into a web with a carding machine. Layer 2 minimally contains heat-fusing short fibers where 50% or more are hydrophilic fibers. Said fibers are also formed into a web with a carding machine. The webs of Layer 1 and Layer 2 that have been obtained in this manner are either laminated after forming fiber aggregates by fusing with separate heating rollers or heating fluids, or the webs of Layer 1 and Layer 2 are laminated and then simultaneously formed into fiber aggregates by fusing using a heating roll or heating fluid. Following this, by passing the fiber aggregates in the laminated state through an ultrasonic wave type or heating roll type engraving roll and partially compression bonding and/or fusing, they are given so-called embossing. In this embossing, an arbitrary embossed pattern is formed which possesses Section A of which fiber density is comparatively low, Section B of which fiber density is comparatively high and Section C which is located at the boundary of Portions A and B, where the surface area ratio of Section C is 2-50% with respect to the total surface area of the embossing.

Further, in this invention, embossing is performed on Layer 1 for at least the portion which covers Layer 2. In portions where Layer 2 is not present and is composed of Layer 1 only, embossing may or may not be performed.

The following provides a detailed description of the differences between conventional surface materials and the surface material of this invention based on the accompanying diagrams.

Figure 1:
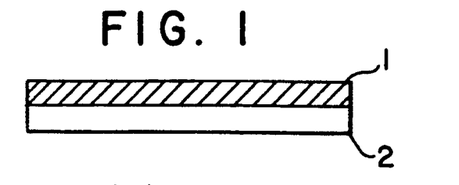
FIGS. 1-3 are cross-sectional diagrams which indicate conventional surface material of the prior art.
Figure 2:
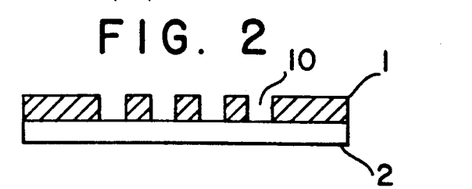
Figure 3:
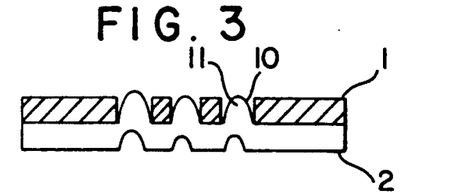

FIGS. 1-3 are cross-sectional diagrams showing conventional surface materials, and FIGS. 4-7 are cross-sectional diagrams which show each of the embodiments of the surface material of this invention.

The conventional surface material indicated in FIG. 1 is such that Layer 1, which is composed of hydrophobic fibers that are located on the surface in contact with the skin, and Layer 2, which is composed of hydrophilic fibers lying beneath Layer 1, are formed into a single unit, and the fiber density of Layer 1 is essentially uniform. In this type of composition, although there is a high degree of backflow prevention when the thickness of Layer 1 is comparatively large, it has poor liquid permeability. In the case the thickness of Layer 1 is comparatively small, in contrast, although it has ample liquid permeability, backflow prevention is poor. If the thickness of Layer 1 is of an intermediate thickness, both liquid permeability and backflow prevention become inadequate, and in either case, the co-existence of both liquid permeability and backflow prevention is fundamentally impossible.

On the other hand, although the conventional surface material indicated in FIG. 2 is also composed by forming hydrophobic Layer 1 (1), which is located on the surface in contact with the skin, into a single unit with hydrophilic Layer 2 beneath Layer 1, in the surface material indicated in FIG. 3 in which holes (10) are provided in hydrophilic layer 1, in addition to this, hydrophilic Layer 2 penetrates to the surface of hole portion (10) in the manner of (11). In this type of composition, as was described previously, when pressure is applied due to movement by the user, since liquid that has migrated to the absorber easily transfers to the body surface from holes (10), the surface material that is obtained has inadequate backflow prevention.

In contrast to this, the surface material of this invention is composed of Layer 1 (1), which is located on the surface in contact with the skin, and Layer 2 (2), which is formed into a single unit with Layer 1 (1) located beneath Layer 1 (1) such that its entire surface is essentially covered by Layer 1 (1). Layer 2 (2) is composed of 50% or more hydrophilic fibers. Section A (3) of which the fiber density is comparatively low, Section B (4 of which the fiber density is comparatively high, and Section C (5) which is located at their boundary exist in Layer 1 (1). Although the surface layer of Section A (3) is at a considerable distance from hydrophilic Layer 2 (2) and has superior backflow prevention, since its fiber density is low and it has ample porosity, it possesses some degree of liquid permeability. In addition, although Section B (4) has extremely superior backflow prevention due to it having high fiber density with the fibers existing close to one another resulting in low porosity, it essentially has no liquid permeability. Section C (5) is located at the boundary between Section A (3) and Section B (4), and since the fiber density is intermediate while its surface layer is at a small distance from hydrophilic Layer 2, although it has extremely superior liquid permeability, it has poor backflow prevention.

According to this invention, by making the proportion of the area of this type of Section C to the total area of the surface material (referred to as the surface ratio of the Section C, refer to the embodiments for the method of measurement) 2-50%, it becomes possible for the first time to obtain a surface material having both superior liquid permeability and backflow prevention characteristics. If the surface area ratio of Section C is less than 2%, the necessary degree of permeability will not be able to be obtained, and if it exceeds 50%, the necessary degree of backflow prevention will be unable to be obtained. Therefore, these will not fulfill the intentions of this invention.

Figure 8:
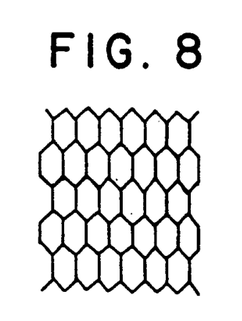
FIGS. 8-11, 12(a), 12(b), 13(a), 13(b) are front views which indicate the surface material of this invention.
Figure 9:
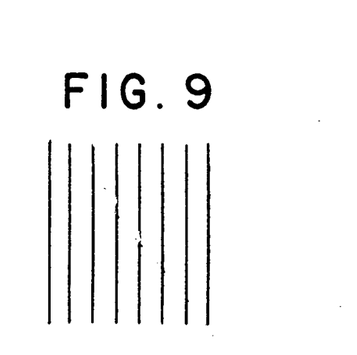

The desirable value for the surface area of Section C varies according the planar form, etc. of the surface material. For example, in the case Section B is in the form of lines as is indicated in FIGS. 8 and 9, a value of 2-20% is preferable with a value of 2-10% being more preferable. In addition, in the case Section B is in the form of dots as is indicated in FIGS. 10 and 11, a value of 10-40% is preferable with a value of 20-35% being more preferable.

Figure 10:
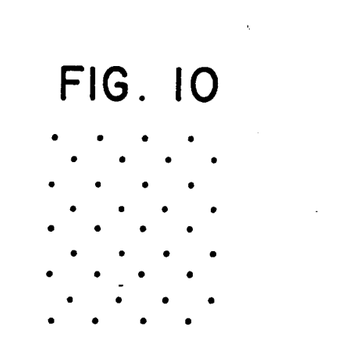
Figure 11:
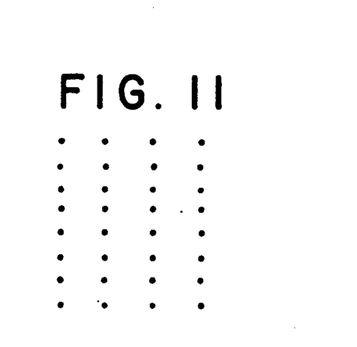

Although it is possible for Section B to be in the form of lines as indicated in FIGS. 8 and 9 with the surface material having a planar form, in consideration of ventilation, it is preferable that Section B is in the form of dots as indicated in FIGS. 10 and 11.

If the weighting of Layer 1 and Layer 2 is essentially uniform, the fiber density of Layer 1 is uniquely controlled by the thickness of the surface material. The greater the thickness of the surface material, the lower the fiber density, and the smaller the thickness of the surface material, the greater the fiber density. Since a thickness which provides preferable fiber density for each of the Portions A, B and C varies according to the type of fiber that is used, etc., such thickness is not strictly limited. However, in general, a thickness of 0.2–2.0 mm for Section A is preferable, with 0.3–1.0 mm being more preferable and 0.3–0.6 mm being even more preferable. In addition, a thickness of 0.01–0.30 mm for Section B is generally preferable, with 0.02–0.20 mm being more preferable, and 0.03–0.06 mm being even more preferable. Further, a thickness that is intermediate to the thicknesses indicated above is preferable for Section C. If Sections A and B are too thin, backflow prevention will be reduced and conversely, if they are too thick, liquid permeability will be poor. Thus, neither of these conditions is preferable. In addition, if Section A is too thin, since parts of Layer 2 will be exposed to the surface, backflow prevention will be lowered. Conversely, if Section A is too thick, since the liquid permeability of Section C will be decreased, both of these conditions also are not preferable.

The following provides a detailed description regarding Layers 1 and 2 of this invention.

Although Layer 1 requires that it contain at least 50% hydrophobic fibers, in consideration of backflow prevention, it is more preferable that it is composed only of hydrophobic fibers. In the case the amount of hydrophobic fibers is less than 50%, although Layer 1 will have increased wetness and favorable moisture absorption, when used as the surface material of a sanitary article, the sense of dryness of the surface will be impaired.

Although the type of hydrophobic fiber that is used is not subject to any particular limitations allowing selection to be made freely from commonly known types such as polyolefine, polyester, acrylic and polyamide fibers, in consideration of heat processing properties and ventilation, polypropylene, polyester, polyethylene-polypropylene compound fibers, polyethylene-polyester compound fibers, and low melting point polyester-polyester compound fibers are preferable. Although such hydrophobic fibers can be used as is without treating, in consideration of ease of processing, it is preferable that for example, such fibers are treated with antistatic substances such as fluoride compounds having water repelling capability, paraffin-based waxes, or alkylphosphate metal salts, etc. Although such antistatic substances may be of slight hydrophilic nature, it is necessary to determine the composition and amount applied so that the hydrophilic nature of Layer 1 does not exceed that of Layer 2. In consideration of liquid permeability and ventilation, fiber width of 0.3–10d is generally preferable, with 2–4d being more preferable.

Figure 4:
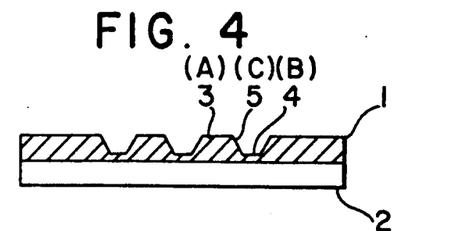
FIGS. 4-7 are cross-sectional diagrams which indicate embodiments of the surface material of this invention.
Figure 6:
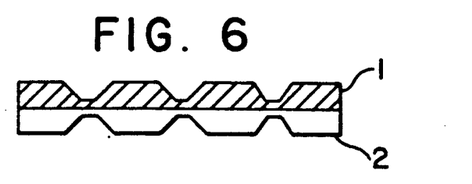
Figure 7:
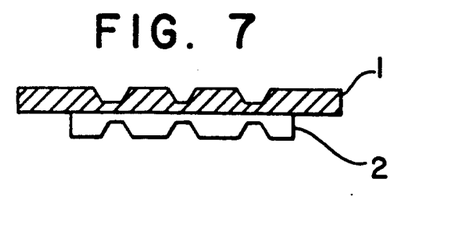

Although the planar form of Section A may be such that the surface layer is flat, if it is depressed at Sections B and C as in FIGS. 4, 6 and 7, since contact of the skin of the user with Section B, which has high rigidity and is a factor causing poor ventilation, as well as Section C, which has poor backflow prevention, is prevented, this is extremely desirable.

Weighting of Layer 1 should be established giving consideration to liquid permeability and backflow prevention In general, weighting of 5–50 g/m$^2$ is preferable, and more preferable if 10–25 g/m$^2$.

When considering staining prevention, it is preferable that the fibers of Layer 1 be opaque. If the fibers are opaque, the surface material of this invention will also be opaque. Since this will allow the surface material to effectively cover up the colors of adhered liquids such as blood or fecal material, stain prevention will be improved. Although the opaqueness of this surface material is quantified in terms of whiteness (see Embodiments), it is preferable that such whiteness be 20% or more, with 30% or more being more preferable. Furthermore, various methods can be considered for giving the desired degree of opaqueness. An example of such method involves adding white pigment to the resin in the fiber manufacturing process. However, as long as it is possible to give the desired degree of opaqueness, any method may be used without being limited to methods like that above. In addition, in the case of using compound fibers such as polyethylene-polypropylene compound fibers or polyethylene-polyester compound fibers, it is preferable to make the white pigment ubiquitous in high melting temperature resin within the fibers since this effectively improves stain prevention.

In order to prevent tearing or unraveling of the surface material, it is preferable that the fibers of Layer 1 are sufficiently intertwined, or depending on the case, adhered to each other in the same manner as nonwoven fabric of conventional absorbent products. Although intertwining can be performed by high pressure fluids and adhesion performed using an adhesive or thermal adhesion, thermal adhesion is more preferable in consideration of liquid permeability and ventilation. Incidentally, adhesion may be performed uniformly within Layer 1 or distributed regularly or irregularly.

On the other hand, although Layer 2 requires that it contain at least 50% hydrophilic fibers, in consideration of liquid permeability, it is preferable that it consists of hydrophilic fibers only.

Although fibers composed of hydrophilic substances such as pulp or rayon, as well as fibers in which the surfaces of fibers composed of hydrophobic substances such as polyolefine, polyester, acrylic or polyamide fibers which have undergone hydrophilic treatment using suitable methods, can be used for the hydrophilic fibers, in consideration of backflow prevention and ventilation, the latter are preferable. From among these, in consideration of ease of heat processing and ventilation, those in which the surface of polypropylene, polyester, polyethylene-propylene compound fibers, polyethylene-polyester compound fibers or low melting point polyester-polyester compound fibers have undergone hydrophilic treatment similar to those of Layer 1 are more preferable. In other words, hydrophilic fibers refers to fibers in which a surface active agent possessing hydrophilic function, such as the ethylene oxide adduct of sulfonic acid chloride or the ethylene oxide addition product of sulfuric ester chloride, is added to said thermoplastic fiber, or fibers which are hydrophilic by nature such as rayon or cotton. In the case the amount of hydrophilic fibers is less than 50%, the wetting and absorption properties of Layer 2 will be reduced excessively such that when used as the surface material of a sanitary article, liquid absorption will be decreased remarkably due to Layer 1 being composed of 50% or more hydrophilic fibers. In consideration of backflow prevention and ventilation, a fiber width of 0.3–10d is preferable, with 2–4d being more preferable.

The weighting of Layer 2 also should be established in consideration of liquid permeability and backflow prevention. In general, 10–50 g/m² is preferable, with 15–40 g/m² being more preferable.

In addition, in the same manner as Layer 1, it goes without saying that opaque fibers should be used in order to improve stain prevention.

Figure 5:
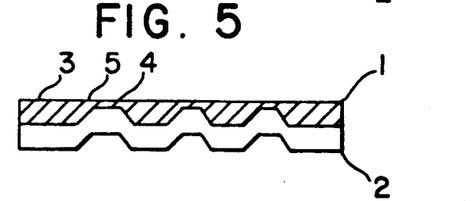

Although the thickness of Layer 2 may be essentially uniform as in FIGS. 4 and 5, it is more preferable if the thickness of Layer 2 is made thinner beneath Sections A and C of Layer 1 as in FIGS. 6 and 7 since this results in increased liquid diffusivity thereby improving the liquid permeability of the surface material. In addition, although it is possible to make all of Layer 2 exist beneath Layer 1 as in FIGS. 4–6, it is extremely desirable if it is made to exist only at the central portion of Layer 1 as in FIG. 7 since diffusion of liquid at both edges of the surface material is reduced resulting in a dramatic improvement in leakage prevention.

Although it is required that Layers 1 and 2 be formed into a single unit, it is preferable that they are formed into a single unit to such a degree such that they at least do not come apart during use. Although examples of methods to accomplish this include thermal adhesion by hot air treatment, etc., thermocompression bonding by thermal embossing or ultrasonic embossing, etc., adhesion using an adhesive and intertwining using an air flow or high pressure water flow, in consideration of ventilation and productivity, etc., it is preferable to form Sections B and C on Layer 1 by ultrasonic embossing treatment after first performing thermal adhesion of Layer 1 and Layer 2 using hot air treatment.

In the preparing method of this invention, the purpose of performing so-called embossing by laminating Layers 1 and 2 and passing them through an ultrasonic wave type or heating roll type of engraving roll followed by partial compression bonding and/or fusing is that liquid absorption would be low or completely absent if the layers were simply laminated only due to Layer 1 being essentially hydrophobic and Layer 2 being essentially hydrophilic. As such, the inventors discovered that liquid absorption would be exhibited by making the layers thinner in parts by embossing in a laminated state.

Although the mechanism of this is not clear, it is believed that liquid absorption is exhibited by shortening the distance in the thickness direction between essentially hydrophobic Layer 1 and essentially hydrophilic Layer 2. In actuality, liquid absorption is demonstrated remarkably in Section C at the boundary of Section B, which is compression bonded and/or fused and has comparatively high fiber density, and Section A, which is not compression bonded and/or fused and has comparatively low fiber density. Therefore, since if the weighting of Layer 1 is too high, liquid absorption decreases, and conversely, if it is too low, liquid backflow occurs easily, weighting of 10–25 g/m² is preferable. On the other hand, since if the weighting of Layer 2 is too high, liquid retention is increased and backflow occurs easily, weighting of 10–25 g/m² is preferable.

In this invention, a pattern is selected and used which possesses Section A, which has comparatively low fiber density, Section B, which has comparatively high fiber density, and Section C, which is at the boundary between them, by compression bonding and/or fusing so that the surface area ratio of Section C is 2–50% with respect to the total surface area of the embossing. In the case said surface area ratio is less than 2%, liquid absorbing portions are too few causing liquid absorption to become extremely poor. In addition, if said surface area is greater than 50%, although liquid absorption is favorable, since the thickness of the surface material becomes extremely thin and moreover, due to reduced ventilation, on the contrary, liquid backflow becomes worse.

Examples of embossing methods include a method in which one or both rolls pass through an opposing heating roll having an engraving pattern which satisfies the above surface area ratio, and a method in which one or both rolls pass between a non-heating engraving roll having the above pattern and an ultrasonic oscillation horn.

In regard to the preferable form of the preparing method of this invention, in order to inhibit and prevent the leakage of absorbed liquid in the horizontal direction, the web of Layer 2 is suctioned and removed at fixed intervals with respect to the horizontal direction prior to lamination of Layer 1 and Layer 2 with respect to the direction of flow of the fiber aggregates. Following lamination, a slit is made in the center of the formed portion which is essentially Layer 1 only followed by winding. The nonwoven fabric that is prepared in this manner following slitting is able to inhibit and prevent staining and leakage in the horizontal direction when using in the surface materials of sanitary articles since Layer 2 does not exist at a fixed width on both ends in the horizontal direction and both ends are essentially formed from hydrophobic fibers. In contrast to the web width of ordinary nonwoven fabric production machines being on the order of 1–2.5 m, since the width when used in the surface materials of sanitary articles is on the order of 0.1–0.5 m, a multiple number of rolls are produced as surface materials of sanitary articles. Therefore, the web of Layer 2 is removed at a multiple number of locations at fixed intervals with respect to the horizontal direction. Examples of methods which can be used for the above web removal method for Layer 2 include a method in which a metallic wire wound onto a carding roller is wound at fixed intervals in the horizontal direction, a method in which following forming of the web over the entire width of the carding, the web is removed by suctioning while simultaneously cutting at fixed intervals with a slitter, and a method in which while holding down the web at fixed intervals with a plate on a roller at the outlet of the carding machine, the portions of the web that are not being held down are removed by suctioning.

Figure 18:
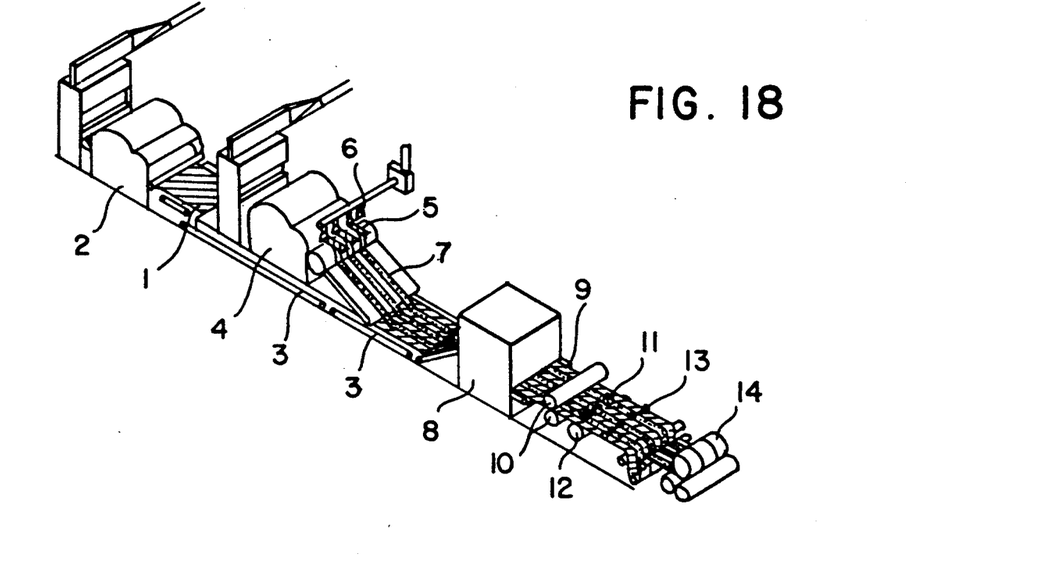
FIG. 18 is an oblique angle diagram of one example of the equipment used in the preparing method of this invention. The figures will be explained in more detail below.

The following is a detailed description of one of the preparing methods as indicated in FIG. 18. Web (1) which forms Layer 1 comes out of carding machine #1 (2) and moves onto conveyor (3). Continuing, the web of Layer 2 is formed from carding machine #2 (4). Providing a multiple number of plates (5) of fixed width on the roller at the outlet of carding machine #2 (4) at fixed intervals, the portions of the web which are not being held down with said plates are suctioned and removed with suction nozzles (6). It is preferable that the web that has been suctioned and removed be returned again to the entrance of carding machine #2 from the viewpoint of reducing loss of raw stock. Then, web (1), which forms Layer 1, and web (7), which is remaining after suction and removal and forms Layer 2, are laminated to form sheet (9) by passing through hot air chamber (8) to fuse the fibers. Following this, embossing is performed by passing through calender rollers (10) and between ultrasonic wave generator horn (11) and engraving roll (12). The center of the portion of Layer 1 only is cut with slitter (13) after which the laminated material is wound into roll form (14).

Although the following provides a description of the surface material of this invention using the example of disposable diapers, this invention is not limited to these embodiments, but can also be applied for use in other sanitary articles such as sanitary napkins and sanitary pads.

The surface materials indicated in Table 1 and Table 2 were prepared with the specified methods using the component materials indicated in Table 1. The following describes the measurement methods for shape and performance of each of the surface materials. Furthermore, the values indicated in Table 1 and Table 2 are the average values of 10 measured values.

(1) Shape (i) Dimensions of Each Section

Figure 15:
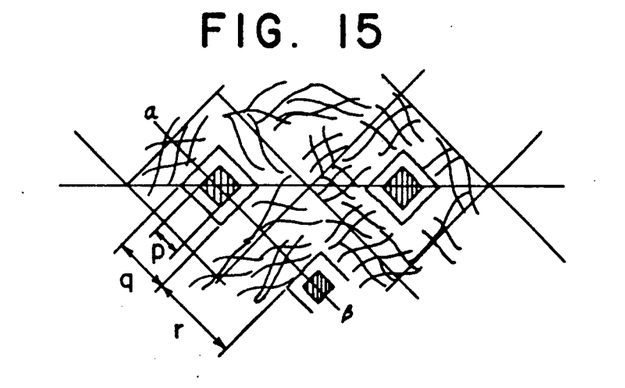
FIG. 15 is a top view of the surface material in order to determine the dimensions of each section of the embossing pattern.

Photographs of the flat and cross-sectional surfaces of the surface materials (embossed portions) were taken using a scanning electron microscope. The length p of the embossed portion in the photographs as well as the length q of the periphery of the embossed portions were measured (Top View: FIG. 15). In addition, straight lines $l_1$ and $l_2$ in cross-sectional diagrams FIGS. 16 and 17 essentially define the thickness $t_1$ of the embossed portion (fiber compression bonding portion). Next, the thickness $t_2$ of the fiber non-compression bonding portion is determined according to straight lines $l_7$ and $l_8$ which are essentially tangent to the flat portion. Further, straight lines $l_3$ and $l_4$ are erected from both ends of the fiber compression bonding portion in a direction perpendicular to straight line $l_2$, and similarly, straight lines $l_5$ and $l_6$ are erected from both ends of the fiber non-compression bonding portion in a direction perpendicular to straight line $l_7$. At this time, the distance between lines $l_3$ and $l_4$ expresses the dimensions of b, the distance between lines $l_4$ and $l_5$ expresses the dimensions of c, and the distance between lines $l_5$ and $l_6$ expresses the dimensions of a. In addition, the distance which connects intersection point $C_1$ of lines $l_4$ and $l_2$ and intersection point $C_2$ of lines $l_5$ and $l_7$ is taken to be d.

(ii) Surface Area Ratio of Section C

Figure 16:
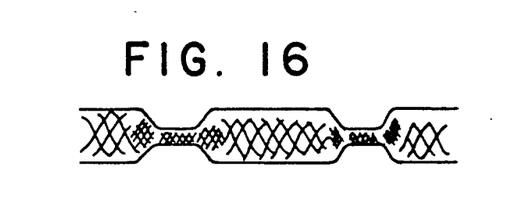
FIG. 16 is a cross-sectional diagram of the surface material in FIG. 15.
Figure 17:
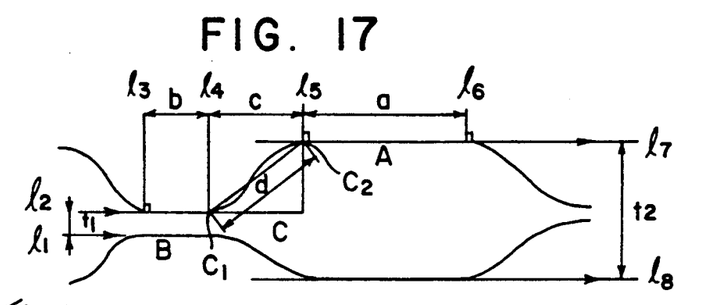
FIG. 17 is an enlarged diagram of FIG. 16.

The surface area ratio of Section C is calculated using the following equations using the values of each of the portions obtained from (i) above. Surface Area of Fiber Compression Bonding Portion (Section B)

$$M_B = b \cdot p \times 10^3 \ (mm^2)$$

Surface Area of Fiber Non-Compression Bonding Portion (Section A)

$$M_A = a \cdot (a + 2b + 3c) \times 10^3 \ (mm^2)$$

Surface Area of Middle Portion (Section C)

$$M_C = 2 \ (p+q) \cdot d \times 10^3 \ (mm^2)$$

Surface Area Ratio of Section C:

$$\frac{M_C}{M_A + M_B + M_C} \ (\%) = \frac{2(p+q)d}{a^2 + b(2ab + p) + 3ca + 2(p+q)d}$$

(2) Performance

Figure 12A:
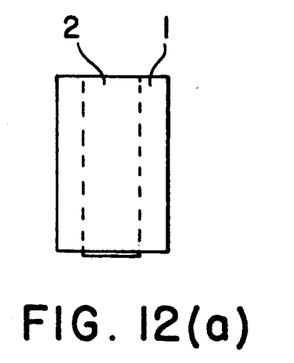
Figure 12B:
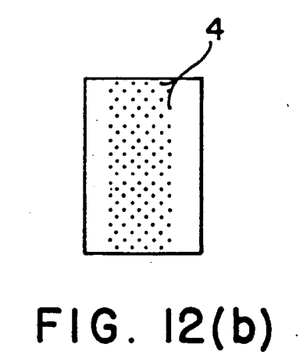
Figure 13A:
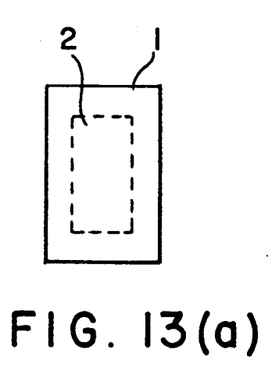
Figure 13B:
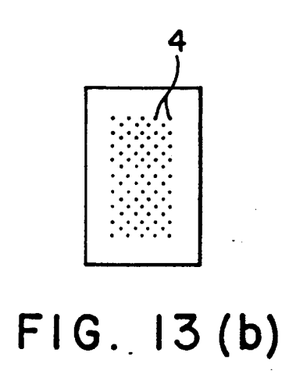

At the time of evaluation, the surface material of a commercially available disposable diaper, Merries of Kao Corporation was removed and replaced with each of the surface materials to be evaluated. These were then evaluated as the hypothetical disposable diaper samples. Furthermore, in Embodiment 6, Section B and Section C were formed by superimposing Layer 2 on the central portion of Layer 1 in the horizontal direction and performing ultrasonic wave embossing on the portions where Layer 2 was present as indicated in FIG. 12. In addition, in Embodiment 7, Section B and Section C were formed by superimposing Layer in the central portion of Layer 1 in both the horizontal and vertical directions and performing ultrasonic wave embossing on the portion where Layer 2 was present as indicated in FIG. 13.

(i) Absorption Time and Liquid Backflow Volume

A specified amount of test liquid was injected under pressure onto the hypothetical disposable diaper sample. The amount of time required to absorb the liquid was taken to be the absorption time. In general, the shorter this absorption time, the more superior the liquid permeability of the surface material. Further, the amount of test liquid that flows back from the inside of the sample through the surface material applying high pressure after a fixed amount of time was taken to be the liquid backflow volume. The smaller the liquid backflow volume, the smaller the degree of stickiness of the surface indicating a more pleasant feel when used.

(ii) Stain Prevention

Figure 14:
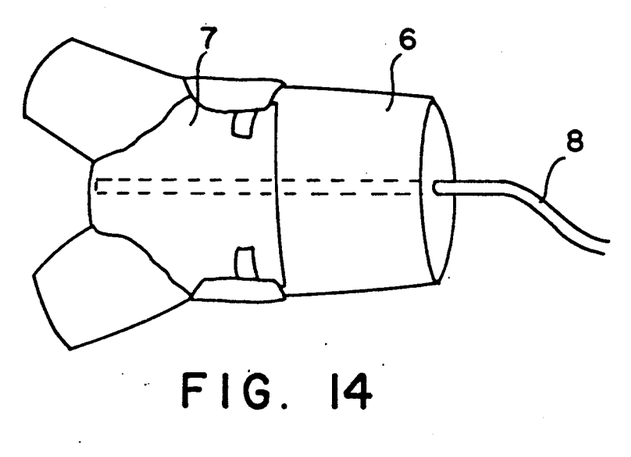
FIG. 14 is a diagram which indicates the method of measurement of maximum absorption volume.

The state of the hypothetical disposable diaper sample was divided into the three ranks indicated below following the absorption of a colored test liquid.
Class 3: Color of test liquid can hardly be observed
Class 2: Color of test liquid is slightly observed
Class 1: Color of test liquid can be observed remarkably to an extent of being unpleasant (iii) Maximum Absorption Volume The maximum absorption volume was taken to be the amount of test liquid injected at the point leakage is observed by placing an infant model (6) horizontally, putting the hypothetical disposable diaper sample (7) on the model and injecting the test liquid from tube (8). The greater this maximum absorption volume, the more superior the stain prevention.

(iv) Ventilation

The feel when a hypothetical napkin sample is touched with the hand divided into the three ranks indicated below.
Class 3: Soft
Class 2: Somewhat stiff
Class 1: Stiff and unsuitable as a surface material The processing agents a and b used in Table 1 are as indicated below.
a: Fiber processing agent of which the main component is alkylphosphate (a is less hydrophilic than b).

b: Fiber processing agent of which the main component is alkylphosphate to which polyethylene glycol has been added.

TABLE 1

| | | Layer 1 | | | | |
|---|---|---|---|---|---|---|
| | | Composition | Processing Agent | Weighting g/m² | Stabilization Method | Dimention mm |
| Embodiments | 1-5, 8 | ES 2d 100% | a | 19 | Thermal Adhesion | 460 × 310 |
| | 6 | " | " | 21 | Thermal Adhesion | " |
| | 7 | " | " | 21 | Thermal Adhesion | " |
| | 9 | " | " | 20 | Thermal Adhesion | " |
| | 10 | ES 2d 70% ESHB 2d 30% | a b | 22 | Thermal Adhesion | " |
| Comparative Example | 1 | ES 2d 50% SH 3d 50% | a b | 35 | Thermal Adhesion | " |
| | 2 | ES 2d 100% | a | 20 | Thermal Adhesion | " |
| | 3 | " | " | 22 | Thermal Adhesion | " |
| | 4-5 | ES 2d 100% | " | 19 | Thermal Adhesion | " |

| | | Layer 2 | | | | Preparation Method | |
|---|---|---|---|---|---|---|---|
| | | Composition | Processing Agent | Weighting g/m² | Stabilization Method | Dimention mm | Unification Method | Forming Method |
| Embodiments | 1-5, 8 | SH 3d 100% | b | 16 | Thermal Adhesion | 460 × 310 | Thermal Adhesion | Ultrasonic Wave Treatment |
| | 6 | " | " | 15 | Thermal Adhesion | 460 × 200 | Thermal Adhesion | Ultrasonic Wave Treatment |
| | 7 | " | " | 16 | Thermal Adhesion | 460 × 200 | Thermal Adhesion | Ultrasonic Wave Treatment |
| | 9 | ESHB 3d 100% | " | 14 | Thermal Adhesion | 460 × 310 | Thermal Adhesion | Ultrasonic Wave Treatment |
| | 10 | SH 3d 100% | " | 15 | Thermal Adhesion | " | Thermal Adhesion | Ultrasonic Wave Treatment |
| Comparative Example | 1 | — | — | — | — | — | — | — |
| | 2 | SH 3d 100% | b | 16 | Thermal Adhesion | 460 × 310 | Thermal Adhesion | — |
| | 3 | " | " | 15 | Thermal Adhesion | 460 × 310 | Thermal Adhesion | — |
| | 4-5 | " | b | 14 | Thermal Adhesion | " | Thermal Adhesion | Ultrasonic Wave Treatment |

(Notes)
ES: Polyethylene-Polypropylene compound fiber (flat crimped type, Chisso Co., Ltd.)
ESHB: Polyethylene-Polypropylene compound fiber (solid crimped type, Chisso Co., Ltd.)
SH: Polyethylene-Polyester compound fiber (flat crimped type, Daiwa Spinning Co., Ltd.)

TABLE 2

| | Shape | | | | Performance | | | | | |
|---|---|---|---|---|---|---|---|---|---|---|
| | Surface Area Ratio of Section C % | Thickness Section A um | Thickness Section B um | Flat Shape | Absorption Time - Second | Backflow Volume g | Staining Prevention - Class | Maximum Absorption Volume g | Ventilation - Class | Remarks |
| Embodiment | | | | | | | | | | |
| 1 | 8 | 462 | 44 | Fig. 10 | 66 | 0.06 | 3 | 115 | 3 | |
| 2 | 28 | 453 | 47 | " | 42 | 0.08 | 3 | 126 | 3 | |
| 3 | 44 | 446 | 51 | " | 38 | 0.25 | 2 | 108 | 2 | |
| 4 | 29 | 460 | 15 | " | 37 | 0.19 | 2 | 105 | 2 | |
| 5 | 30 | 462 | 139 | " | 53 | 0.06 | 3 | 111 | 3 | |
| 6 | 29 | 460 | 50 | " | 43 | 0.08 | 3 | 194 | 3 | |
| 7 | 30 | 462 | 49 | " | 42 | 0.08 | 3 | 253 | 3 | |
| 8 | 4 | 426 | 34 | Fig. 8 | 75 | 0.05 | 3 | 119 | 2 | |
| 9 | 29 | 455 | 51 | Fig. 10 | 43 | 0.11 | 3 | 116 | 3 | |
| 10 | 33 | 469 | 52 | " | 40 | 0.15 | 2 | 103 | 3 | |
| Comp. Ex. | | | | | | | | | | |
| 1 | 0 | — | — | — | 33 | 1.44 | 1 | 52 | 3 | |
| 2 | 0 | — | — | — | 126 | 0.02 | 2 | 67 | 3 | |

TABLE 2-continued

| | Shape | | | Shape and Performance | | Performance | | | |
|---|---|---|---|---|---|---|---|---|---|
| Surface Area Ratio of Section C % | Thickness Section A um | Section B um | Flat Shape | Absorption Time - Second | Backflow Volume g | Staining Prevention - Class | Maximum Absorption Volume g | Ventilation - Class | Remarks |
| 0 | — | — | — | 38 | 1.63 | 1 | 42 | 1 | |
| 1 | 573 | 31 | Fig. 8 | 114 | 0.04 | 2 | 66 | 3 | |
| 65 | 375 | 35 | Fig. 10 | 34 | 0.54 | 2 | 76 | 1 | |

(First column values: 3, 4, 5)

The following indicates embodiments of the preparing method of this invention.

Embodiment 1

Layer 1 was formed by adding 0.3 wt.% hydrophobic surface activating agent of which the main component is alkylphosphate K salt to the surface of 51 mm of 2 denier heat-fusing short fiber of polypropylene-polyethylene core sheath structure (ES Fiber, Chisso Co., Ltd.) and forming a hydrophobic web having a weighting of 20 g/m² with 100% of said fiber using the #1 carding machine. Layer 2 was formed by adding 0.3 wt.% hydrophilic surface activating agent of which the main component is the polyethylene glycol addition product of lauryl ether sodium sulfate to 38 mm of 3 denier heat-fusing short fiber of polyester-polyethylene core sheath structure (NBF Fiber, Daiwa Spinning Co., Ltd.) and forming a hydrophilic web having a weighting of 20 g/m² with 100% of said fiber using the #2 carding machine. Following this, the fibers were fused together by laminating the webs of Layer 1 and Layer 2 and passing through a hot air type, heat treatment machine. Following calender processing, embossing was performed with an ultrasonic wave generation horn and engraving roll in which the surface area ratio of Section C becomes 20% to obtain the nonwoven fabric of the surface material for the disposable diaper. When the performance of said nonwoven fabric was evaluated as a surface material using the absorber of a commercially available disposable diaper (Mary's, Kao Co., Ltd.), the results indicated in Table 3 were obtained.

Surface Liquid Flow (Large): At the time of urination, urine is not absorbed quickly causing it to leak flowing on the surface of the surface material.

(Small): At the time of urination, urine is absorbed quickly and is unable to flow through the surface of the surface material.

Surface Liquid Backflow (Small): The surface material feels dry with hardly any urine flowing back to the surface of the surface material.

(Large) The surface material feels sticky with a large amount of urine flowing back to the surface of the surface material.

Embodiment 12

Layer 1 was formed by adding 0.3 wt.% hydrophobic surface activating agent of which the main component is alkylphosphate K salt to the surface of 38 mm of 2 denier heat-fusing short fiber of polyester-polypropylene core sheath structure (NBF Fiber, Daiwa Spinning Co., Ltd.) and forming a hydrophobic web having a weighting of 23 g/m² with 100% of said fiber using the #1 carding machine. Layer 2 was formed by adding 0.3 wt.% hydrophilic surface activating agent of which the main component is the polyethylene glycol addition product of lauryl ether sodium sulfate to 51 mm of 3 denier heat-fusing short fiber of polyester-polyethylene core sheath structure (NBF Fiber, Daiwa Spinning Co., Ltd.) and forming a hydrophilic web having a weighting of 20 g/m² with 100% of said fiber using the #2 carding machine. Following this, cutting was performed with a web slitter at a pitch of 17 cm of the portion which was not suctioned and removed of the hydrophilic web only and 16 cm of the portion which was suctioned and removed followed by suction and removal. Continuing, the fibers were fused together by laminating the webs of the portions of Layer 1 and Layer 2 that were not suctioned and removed and passing through a hot air type, heat treatment machine. Embossing was performed with an ultrasonic wave generation horn and engraving roll in which the surface area ratio of Section C becomes 15%. The central portion of Layer 1 only was then slit and wound. When the performance of said nonwoven fabric was evaluated as a surface material using the absorber of a commercially available disposable diaper (Mary's, Kao Co., Ltd.), the results indicated in Table 4 were obtained.

TABLE 3

| | Layer 1 | Layer 2 | Embossing | Surface Liquide Flow | Surface Liquid Backflow | Total Evaluation |
|---|---|---|---|---|---|---|
| Embodiment 11 | Hydrophobic | Hydrophilic | Yes | Small | Small | O |
| Comparative Example 6 | " | " | No | Large | Small | X |
| Compartive Example 7 | Hydrophilic | " | No | Small | Large | X |

TABLE 4

| | Layer 1 | Layer 2 | Embossing | Surface Liquide Flow | Surface Liquid Backflow | Liquid Leakage of Guide | Total Evaluation |
|---|---|---|---|---|---|---|---|
| Embodiment 12 | Hydrophobic | Hydrophilic | Yes | Small | Small | Hardly | O |

TABLE 4-continued

|  | Layer 1 | Layer 2 | Embossing | Surface Liquide Flow | Surface Liquid Backflow | Liquid Leakage of Guide | Total Evaluation |
|---|---|---|---|---|---|---|---|
| Comparative Example 8 | " | " | No | Large | Small | any " | X |
| Comparative Example 9 | Hydrophilic | " | No | Small | Large | Yes | X |

As can be understood from Embodiments 1-10, the surface material of this invention has both superior liquid permeability and backflow prevention. In particular, in Embodiments 6 and 7 in which Layer 2 is not present on both ends in the horizontal direction of Layer 1, since diffusion of liquid on the ends is inhibited, leakage prevention is improved phenomenally making it truly an ideal surface material.

In contrast to this, in Comparative Example 1, since the surface material does not have a double-layer structure, liquid backflow prevention is inferior. In Comparative Example 2, although the surface material has a double-layer structure consisting of hydrophobic and hydrophilic materials, since fiber density is essentially uniform, liquid permeability is inferior. In Comparative Example 3, since holes are provided in the upper hydrophobic layer, backflow prevention is inferior. On the other hand, in Comparative Example 4, since the surface area ratio of Section C is less than 2%, liquid permeability is inferior. In Comparative Example 5, since the surface area ratio of Section C is 50% or more, ventilation is poor and backflow prevention cannot be said to be adequate.

Therefore, one would have to say that those surface materials indicated in the comparative examples are still inadequate as surface materials of sanitary articles.

In addition, by using the nonwoven fabric that is provided by the method of this invention as the surface material of sanitary articles, together with realizing rapid absorption of body liquids, there is hardly any backflow of those absorbed body liquids to the surface of the surface material even when pressure is applied to the sanitary article. Thus, a feeling of dryness is maintained at all times and further, oozing and leaking of body liquids which have been absorbed in the horizontal direction of the nonwoven fabric can be inhibited. This allows inhibition and prevention of staining of clothing by body liquids that have been excreted as well as chafing of the skin, thereby resulting in reduction or elimination of the unpleasant feeling that is caused by the use of sanitary articles.

We claim:

1. A surface material for sanitary articles which has the characteristic of being composed of Layer 1, which is located on the surface adapted to be in contact with the skin, and Layer 2, which is formed into a single unit with Layer 1 on the surface opposite of that which is adapted to be in contact with the skin with its entire surface being essentially covered by Layer 1, and with Layer 1 comprising 50 to 100% of hydrophobic fibers and Layers 2 comprising 50 to 100% of hydrophilic fibers, and moreover, in which at least the portion of Layer 1 covering Layer 2 has an embossed structure and possesses a first section having a given fiber density, a second section of which the fiber density is higher than said given fiber density, and a third section which is located at a boundary between said first and second sections, where the area of the third section occupies 2-50% of the area of the entire surface material.

2. The surface material of claim 1, wherein the first section has a thickness of 0.2-2.0 mm, the second section has a thickness of 0.1-0.30 mm, and the third section has an intermediate thickness.

3. The surface material of claim 2, wherein the first section has a thickness of 0.3-1.0 mm, and the second section has a thickness of 0.02-0.20 mm.

4. The surface material of claim 3, wherein the first section has a thickness of 0.3-0.6 mm and the second section has a thickness of 0.03-0.06 mm.

5. The surface material of claim 1, wherein the hydrophobic material is selected from the group consisting of polyolefin, polyester, acrylic and polyamide fibers, and copolymers thereof.

6. The surface material of claim 5 wherein the hydrophobic material is treated with compounds having water repellant capability, paraffin-based waxes or alkyl-phosphate metal salts.

7. The surface material of claim 1, which weighs 5 to 50 g/m$^2$.

8. The surface material of claim 1, wherein the hydrophobic fibers of Layer 1 have a width of 0.3-10 d.

9. The surface material of claim 1, wherein the Layer 1 comprises 100% of hydrophobic fibers.

10. The surface material of claim 1, wherein the Layer 2 comprises 100% of hydrophilic fibers.

11. The surface material of claim 1, wherein the hydrophilic fibers are selected from the group consisting of hydrophobic fibers which have undergone hydrophilic treatment, cotton fibers and rayon fibers.

* * * * *